(12) United States Patent
Rieck et al.

(10) Patent No.: US 7,186,862 B2
(45) Date of Patent: Mar. 6, 2007

(54) MICROBICIDAL AGENTS ON THE BASIS OF BIPHENYLBENZAMIDE DERIVATIVES

(75) Inventors: Heiko Rieck, Foy-lès-Lyon (FR); Ralf Dunkel, Monheim (DE); Hans-Ludwig Elbe, Wuppertal (DE); Ulrike Wachendorff-Neumann, Neuwied (DE); Astrid Mauler-Machnik, Leichlingen (DE); Karl-Heinz Kuck, Langenfeld (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 10/505,360

(22) PCT Filed: Feb. 11, 2003

(86) PCT No.: PCT/EP03/01322

§ 371 (c)(1),
(2), (4) Date: Jan. 13, 2005

(87) PCT Pub. No.: WO03/069995

PCT Pub. Date: Aug. 28, 2003

(65) Prior Publication Data

US 2005/0119347 A1    Jun. 2, 2005

(30) Foreign Application Priority Data

Feb. 23, 2002 (DE) ................. 102 07 773
Apr. 8, 2002 (DE) ................. 102 15 291

(51) Int. Cl.
*C07C 233/65* (2006.01)
*A01N 37/18* (2006.01)

(52) U.S. Cl. .................... 564/184; 514/617
(58) Field of Classification Search ........... 564/184; 514/617
See application file for complete search history.

(56) References Cited

U.S. PATENT DOCUMENTS 4,837,242 A    6/1989   Ohsumi et al. ............ 514/365
5,589,493 A *  12/1996  Eicken et al. ............ 514/355

FOREIGN PATENT DOCUMENTS

| EP | 0 545 099 | 6/1993 |
|----|-----------|--------|
| JP | 9-132567 | 5/1997 |
| JP | 2001-302605 | * 10/2001 |

OTHER PUBLICATIONS

Bull. Korean Chem. Soc., vol. 21, (month unavailable) 2000, pp. 165-166, Nakcheol Jeong et al, "A Facile Preparation of the Fluoroaryl Zinc Halides: an Application to the Synthesis of Diflunisal".

Chem. Pharm. Bull, 40(1), (month unavailable) 1992, pp. 240-244, Kiyoshi Taniguchi et al, "New 2-Aryliminoimidazolidines. II. Synthesis and Antihypertensive Activity of 2-(Biphenylimino)-imidazolidines".

Database CA 'Online! Chemical Abstracts Service, Columbus, Ohio. US; White, G.A.: "Substitued benzanilides: structural variation and inhibition of complex II activity in mitochondria from a wild-type strain and a carboxin-selected mutant strain of *Ustilago maydis*" retrieved from STN Database accession No. 106:191006 XP002239592 Zusammenfassung & Pesticide Biochemistry and Physiology (1987), 27(3), 249-60.

* cited by examiner

*Primary Examiner*—Shailendra Kumar
(74) *Attorney, Agent, or Firm*—Richard E. L. Henderson

(57) ABSTRACT

The present invention relates to novel microbicidal compositions based on biphenylbenzamide derivatives of the formula (I)

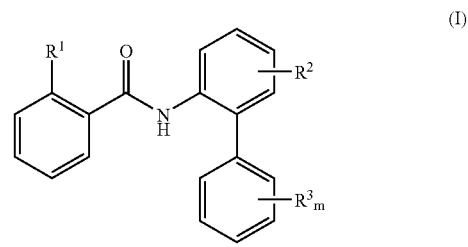

(I)

in which $R^1$, $R^2$, $R^3$ and m are as defined in the disclosure, to novel biphenylbenzamides, to a plurality of processes for preparing these substances and their use for controlling pests, and to novel intermediates and processes for their preparation.

5 Claims, No Drawings

MICROBICIDAL AGENTS ON THE BASIS OF BIPHENYLBENZAMIDE DERIVATIVES

The present patent application has been filed under 35 U.S.C. 371 as a national stage application of PCT/EP03/01322, filed Feb. 11, 2003, which was published in German as International Patent Publication WO 03/069995 on Aug. 28, 2003, and is entitled to the right of priority of German Patent Applications 102 07 773.8, filed Feb. 23, 2002, and 102 15 291.8, filed Apr. 8, 2002.

The present invention relates to novel microbicidal compositions based on biphenylbenzamide derivatives, some of which are known, and to the use of these substances for controlling unwanted microorganisms. Moreover, the invention also relates to novel biphenylbenzamide derivatives and to a plurality of processes for their preparation.

It is already known that biphenylbenzamide derivatives can be employed for controlling species of the phytopathogenic fungus Botrytis (cf. EP-A 0 545 099). However, the activity of these prior-art compounds is, in particular at low application rates, not in all areas of use entirely satisfactory.

Furthermore, certain biphenylbenzamide derivatives such as, for example, the compounds N-(2'-fluoro-1,1'-biphenyl-2-yl)-2-(trifluoromethyl)benzamide and N-(4'-fluoro-1,1'-biphenyl-2-yl)-2-(trifluoromethyl)benzamide (cf. EP-A 0 545 099) are known.

Hitherto, nothing has been disclosed about whether these compounds are suitable for broad fungicidal use. Furthermore, it is not known to what extent these compounds can be used against other microbial, for example bacterial, pests.

It has now been found that the biphenylbenzamide derivatives, some of which are known, of the formula (I)

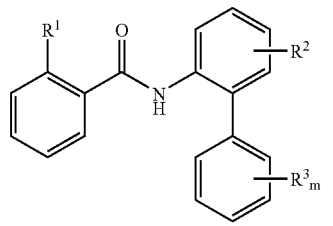

(I)

in which
$R^1$ represents methyl, trifluoromethyl, chlorine, bromine or iodine,
$R^2$ represents hydrogen or fluorine,
$R^3$ represents halogen, cyano, nitro, $C_1$–$C_6$-alkyl, $C_1$–$C_4$-alkoxy, $C_1$–$C_4$-alkylthio, $C_1$–$C_4$-alkylsulphonyl, $C_2$–$C_6$-alkenyl, $C_3$–$C_6$-cycloalkyl, or represents $C_1$–$C_6$-haloalkyl, $C_1$–$C_6$-haloalkoxy, $C_1$–$C_6$-haloalkylthio or $C_1$–$C_6$-haloalkylsulphonyl having in each case 1 to 13 halogen atoms,
m represents 1, 2, 3, 4 or 5, where the radicals $R^3$ may be identical or different if m represents 2, 3, 4 or 5, are highly suitable for controlling phytopathogenic pathogens from the class of the Chytridiomycetes (subdivision of the Mastigomycotina), the class of the Zygomycetes (Zygomycotina), the class of the Hemiascomycetes, Plectomycetes, Pyrenomycetes, Laboulbeniomycetes, Locoloascomycetes (Ascomycotina), and from the subdivisions of the Basidiomycotina and the Deuteromycotina, and also harmful microorganisms in the protection of materials.

Depending on the nature of the substituents, the compounds of the formula (I) can be present as geometrical and/or optical isomers or isomer mixtures of varying compositions. The invention relates both to the use of the pure isomers and to that of the isomer mixture.

The formula (I) provides a general definition of the biphenylbenzamide derivatives which can be used according to the invention.

Preference is given to using biphenylbenzamide derivatives of the formula (I), in which
$R^1$ represents trifluoromethyl, chlorine, bromine or iodine,
$R^2$ represents hydrogen or fluorine,
$R^3$ represents halogen, $C_1$–$C_4$-alkyl, $C_1$–$C_4$-alkoxy, $C_1$–$C_4$-alkylthio, $C_2$–$C_4$-alkenyl, cyclopropyl, cyclobutyl, cyclopentyl, cyclohexyl, or represents $C_1$–$C_4$-haloalkyl, $C_1$–$C_4$-haloalkoxy or $C_1$–$C_4$-haloalkylthio having in each case 1 to 9 halogen atoms,
m represents 1, 2, 3, where the radicals $R^3$ may be identical or different if m represents 2 or 3.

Particular preference is given to using biphenylbenzamide derivatives of the formula (I), in which
$R^1$ represents trifluoromethyl or iodine,
$R^2$ represents hydrogen,
$R^3$ represents fluorine, chlorine, bromine, iodine, methyl, ethyl, n-, i-propyl, n-, i-, s-, t-butyl, methoxy, ethoxy, methylthio, ethylthio, or represents $C_1$–$C_2$-haloalkyl, $C_1$–$C_2$-haloalkoxy or $C_1$–$C_2$-haloalkylthio having in each case 1 to 5 halogen atoms,
m represents 1, 2, where the radicals $R^3$ may be identical or different if m represents 2.

Very particular preference is given to using biphenylbenzamide derivatives of the formula (I), in which
$R^1$ represents trifluoromethyl or iodine,
$R^2$ represents hydrogen,
$R^3$ represents fluorine, chlorine, bromine, methyl, methoxy, methylthio, trifluoromethyl, trifluoromethoxy or trifluoromethylthio,
m represents 1, 2, where the radicals $R^3$ may be identical or different if m represents 2.

Very particular preference is furthermore given to using compounds of the formula (I), in which $R^1$ represents trifluoromethyl.

Very particular preference is furthermore given to using compounds of the formula (I), in which $R^1$ represents iodine.

Very particular preference is furthermore given to using compounds of the formula (I), in which $R^2$ represents hydrogen.

Very particular preference is furthermore given to using compounds of the formula (I), in which $R^2$ represents fluorine.

Very particular preference is furthermore given to using compounds of the formula (I), in which $R^3$ represents fluorine, chlorine or bromine.

Very particular preference is furthermore given to using compounds of the formula (I), in which $R^3$ represents trifluoromethyl, trifluoromethoxy or trifluoromethylthio.

Very particular preference is furthermore given to using compounds of the formula (I), in which m represents 2.

The biphenylbenzamide derivatives of the formula (I) which can be used according to the invention are highly suitable for controlling phytopathogenic pathogens of the classes Chytridiomycetes, Zygomycetes, Hemiascomycetes, Plectomycetes, Pyrenomycetes, Laboulbeniomycetes, Locoloascomycetes, Basidiomycetes and Deuteromycetes, and harmful microorganisms in the protection of materials, such as *Pseudomonadaceae, Rhizobiaceae, Enterobacteriaceae, Corynebacteriaceae* and *Streptomycetaceae*.

Some pathogens causing fungal and bacterial diseases which come under the generic names listed above may be mentioned by way of example, but not by way of limitation
Xanthomonas species, such as, for example, Xanthomonas campestris pv. oryzae;
Pseudomonas species, such as, for example, Pseudomonas syringae pv. lachrymans;
Erwinia species, such as, for example, Erwinia amylovora;
Erysiphe species, such as, for example, Erysiphe graminis;
Sphaerotheca species, such as, for example, Sphaerotheca fuliginea;
Podosphaera species, such as, for example, Podosphaera leucotricha;
Venturia species, such as, for example, Venturia inaequalis;
Pyrenophora species, such as, for example, Pyrenophora teres or P. graminea (conidia form: Drechslera, syn: Helminthosporium);
Cochliobolus species, such as, for example, Cochliobolus sativus (conidia form: Drechslera, syn: Helminthosporium);
Uromyces species, such as, for example, Uromyces appendiculatus;
Puccinia species, such as, for example, Puccinia recondita;
Tilletia species, such as, for example, Tilletia caries;
Ustilago species, such as, for example, Ustilago nuda or Ustilago avenae;
Pellicularia species, such as, for example, Pellicularia sasakii;
Pyricularia species, such as, for example, Pyricularia oryzae;
Fusarium species, such as, for example, Fusarium culmorum;
Septoria species, such as, for example, Septoria nodorum;
Leptosphaeria species, such as, for example, Leptosphaeria nodorum;
Cercospora species, such as, for example, Cercospora canescens;
Alternaria species, such as, for example, Alternaria brassicae;
Pseudocercosporella species, such as, for example, Pseudocercosporella herpotrichoides.

Preferably, the compounds of the formula (I) can be used according to the invention to control the following pathogens causing fungal and bacterial diseases:
Pseudomonas species, such as, for example, Pseudomonas syringae pv. lachrymans;
Erysiphe species, such as, for example, Erysiphe graminis;
Sphaerotheca species, such as, for example, Sphaerotheca fuliginea;
Podosphaera species, such as, for example, Podosphaera leucotricha;
Venturia species, such as, for example, Venturia inaequalis;
Pyrenophora species, such as, for example, Pyrenophora teres or P. graminea (conidia form: Drechslera, syn: Helminthosporium);
Cochliobolus species, such as, for example, Cochliobolus sativus (conidia form: Drechslera, syn: Helminthosporium);
Uromyces species, such as, for example, Uromyces appendiculatus;
Puccinia species, such as, for example, Puccinia recondita;
Tilletia species, such as, for example, Tilletia caries;
Ustilago species, such as, for example, Ustilago nuda or Ustilago avenae;
Pellicularia species, such as, for example, Pellicularia sasakii;
Pyricularia species, such as, for example, Pyricularia oryzae;
Septoria species, such as, for example, Septoria nodorum;
Leptosphaeria species, such as, for example, Leptosphaeria nodorum;
Cercospora species, such as, for example, Cercospora canescens;
Alternaria species, such as, for example, Alternaria brassicae;
Pseudocercosporella species, such as, for example, Pseudocercosporella herpotrichoides.

Particularly preferably, the compounds of the formula (I) can be used according to the invention to control the following pathogens causing fungal and bacterial diseases:
Sphaerotheca species, such as, for example, Sphaerotheca fuliginea;
Podosphaera species, such as, for example, Podosphaera leucotricha;
Venturia species, such as, for example, Venturia inaequalis;
Uromyces species, such as, for example, Uromyces appendiculatus;
Puccinia species, such as, for example, Puccinia recondita;
Pellicularia species, such as, for example, Pellicularia sasakii;
Cercospora species, such as, for example, Cercospora canescens;
Alternaria species, such as, for example, Alternaria brassicae.

Some of the biphenylbenzamide derivatives of the formula (I) which can be used according to the invention are known (cf. EP-A 0 545 099).

The biphenylbenzamide derivatives of the formula (Ia) (group 1)

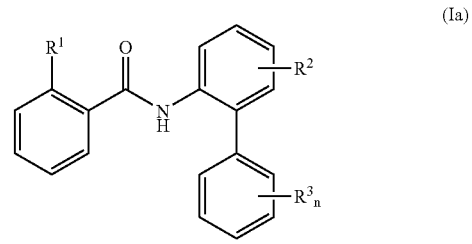

(Ia)

in which
$R^1$ represents methyl, trifluoromethyl, chlorine, bromine or iodine,
$R^2$ represents hydrogen or fluorine,
$R^3$ represents halogen, cyano, nitro, $C_1$–$C_6$-alkyl, $C_1$–$C_4$-alkoxy, $C_1$–$C_4$-alkylthio, $C_1$–$C_4$-alkylsulphonyl, $C_2$–$C_6$-alkenyl, $C_3$–$C_6$-cycloalkyl, or represents $C_1$–$C_6$-haloalkyl, $C_1$–$C_6$-haloalkoxy, $C_1$–$C_6$-haloalkylthio or $C_1$–$C_6$-haloalkylsulphonyl having in each case 1 to 13 halogen atoms,
n represents 2, 3, 4, or 5, where the radicals $R^3$ may be identical or different, are novel.

Preferred are biphenylbenzamide derivatives of the formula (Ia), in which
$R^1$ represents trifluoromethyl, chlorine, bromine or iodine,
$R^2$ represents hydrogen or fluorine,
$R^3$ represents halogen, $C_1$–$C_4$-alkyl, $C_1$–$C_4$-alkoxy, $C_1$–$C_4$-alkylthio, $C_2$–$C_4$-alkenyl, cyclopropyl, cyclobutyl, cyclopentyl, cyclohexyl, or represents $C_1$–$C_4$-haloalkyl, $C_1$–$C_4$-haloalkoxy or $C_1$–$C_4$-haloalkylthio having in each case 1 to 9 halogen atoms, n represents 2, 3, where the radicals $R^3$ may be identical or different.

Particularly preferred are biphenylbenzamide derivatives of the formula (Ia), in which
$R^1$ represents trifluoromethyl or iodine,
$R^2$ represents hydrogen,
$R^3$ represents fluorine, chlorine, bromine, iodine, methyl, ethyl, n-, i-propyl, n-, i-, s-, t-butyl, methoxy, ethoxy, methylthio, ethylthio, or represents $C_1$–$C_2$-haloalkyl, $C_1$–$C_2$-haloalkoxy or $C_1$–$C_2$-haloalkylthio having in each case 1 to 5 halogen atoms,
n represents 2, where the radicals $R^3$ can be identical or different.

Very particularly preferred are biphenylbenzamide derivatives of the formula (Ia), in which
$R^1$ represents trifluoromethyl or iodine,
$R^2$ represents hydrogen,
$R^3$ represents fluorine, chlorine, bromine, methyl, methoxy, methylthio, trifluoromethyl, trifluoromethoxy or trifluoromethylthio,
n represents 2, where the radicals $R^3$ can be identical or different.

Also novel are biphenylbenzamide derivatives of the formula (Ib) (group 2)

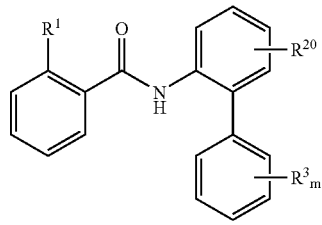

(Ib)

in which
$R^1$ represents methyl, trifluoromethyl, chlorine, bromine or iodine,
$R^{20}$ represents fluorine,
$R^3$ represents halogen, cyano, nitro, $C_1$–$C_6$-alkyl, $C_1$–$C_4$-alkoxy, $C_1$–$C_4$-alkylthio, $C_1$–$C_4$-alkylsulphonyl, $C_2$–$C_6$-alkenyl, $C_3$–$C_6$-cycloalkyl, or represents $C_1$–$C_6$-haloalkyl, $C_1$–$C_6$-haloalkoxy, $C_1$–$C_6$-haloalkylthio or $C_1$–$C_6$-haloalkylsulphonyl having in each case 1 to 13 halogen atoms,
m represents 1, 2, 3, 4 or 5, where the radicals $R^3$ may be identical or different if m represents 2, 3, 4 or 5.

Preferred are biphenylbenzamide derivatives of the formula (Ib), in which
$R^1$ represents trifluoromethyl, chlorine, bromine or iodine,
$R^{20}$ represents fluorine,
$R^3$ represents halogen, $C_1$–$C_4$-alkyl, $C_1$–$C_4$-alkoxy, $C_1$–$C_4$-alkylthio, $C_2$–$C_4$-alkenyl, cyclopropyl, cyclobutyl, cyclopentyl, cyclohexyl, or represents $C_1$–$C_4$-haloalkyl, $C_1$–$C_4$-haloalkoxy or $C_1$–$C_4$-haloalkylthio having in each case 1 to 9 halogen atoms,
m represents 1, 2, 3, where the radicals $R^3$ may be identical or different if m represents 2 or 3.

Particularly preferred are biphenylbenzamide derivatives of the formula (Ib), in which
$R^1$ represents trifluoromethyl or iodine,
$R^{20}$ represents fluorine,
$R^3$ represents fluorine, chlorine, bromine, iodine, methyl, ethyl, n-, i-propyl, n-, i-, s-, t-butyl, methoxy, ethoxy, methylthio, ethylthio, or represents $C_1$–$C_2$-haloalkyl, $C_1$–$C_2$-haloalkoxy or $C_1$–$C_2$-haloalkylthio having in each case 1 to 5 halogen atoms,
m represents 1, 2, where the radicals $R^3$ can be identical or different if m represents 2.

Very particularly preferred are biphenylbenzamide derivatives of the formula (Ib), in which
$R^1$ represents trifluoromethyl or iodine,
$R^{20}$ represents fluorine,
$R^3$ represents fluorine, chlorine, bromine, methyl, methoxy, methylthio, trifluoromethyl, trifluoromethoxy or trifluoromethylthio,
m represents 1, 2, where the radicals $R^3$ can be identical or different if m represents 2.

Also novel are biphenylbenzamide derivatives of the formulae (Ic) (group 3), (Id) (group 4) and (Ie) (group 5)

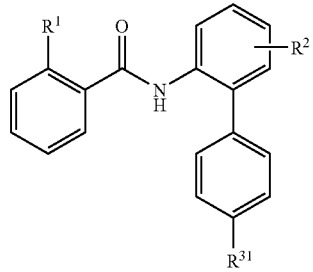

(Ic)

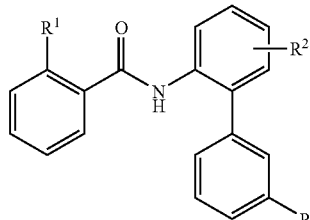

(Id)

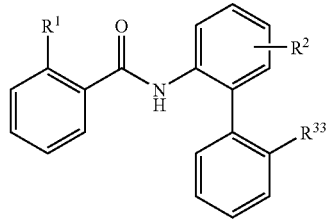

(Ie)

in which in each case
$R^1$ represents methyl, trifluoromethyl, chlorine, bromine or iodine,
$R^2$ represents hydrogen or fluorine,
$R^{31}$, $R^{32}$ and $R^{33}$ independently of one another represent halogen, cyano, nitro, $C_1$–$C_6$-allyl, $C_1$–$C_4$-alkoxy, $C_1$–$C_4$-alkylthio, $C_1$–$C_4$-alkylsulphonyl, $C_2$–$C_6$-alkenyl, $C_3$–$C_6$-cycloalkyl, or represent $C_1$–$C_6$-haloalkyl, $C_1$–$C_6$-haloalkoxy, $C_1$–$C_6$-haloalkylthio or $C_1$–$C_6$-haloalkylsulphonyl having in each case 1 to 13 halogen atoms,
with the proviso that $R^{31}$ and $R^{33}$ each do not represent fluorine if $R^1$ represents trifluoromethyl and $R^2$ represents hydrogen.

Preferred are biphenylbenzamide derivatives of the formulae (Ic), (Id) and (Ie), in which in each case $R^1$ represents trifluoromethyl, chlorine, bromine or iodine,
$R^2$ represents hydrogen or fluorine,
$R^{31}$, $R^{32}$ and $R^{33}$ independently of one another represent halogen, $C_1$–$C_4$-alkyl, $C_1$–$C_4$-alkoxy, $C_1$–$C_4$-alkylthio, $C_2$–$C_4$-alkenyl, cyclopropyl, cyclobutyl, cyclopentyl, cyclohexyl, or represent $C_1$–$C_4$-haloalkyl, $C_1$–$C_4$-haloalkoxy or $C_1$–$C_4$-haloalkylthio having in each case 1 to 9 halogen atoms, with the proviso that $R^{31}$ and $R^{33}$ each do not represent fluorine if $R^1$ represents trifluoromethyl and $R^2$ represents hydrogen.

Particularly preferred are biphenylbenzamide derivatives of the formulae (Ic), (Id) and (Ie), in which in each case $R^1$ represents trifluoromethyl or iodine,
$R^2$ represents hydrogen,
$R^{31}$, $R^{32}$ and $R^{33}$ independently of one another represent fluorine, chlorine, bromine, iodine, methyl, ethyl, n-, i-propyl, n-, i-, s-, t-butyl, methoxy, ethoxy, methylthio, ethylthio, or represent $C_1$–$C_2$-haloalkyl, $C_1$–$C_2$-haloalkoxy or $C_1$–$C_2$-haloalkylthio having in each case 1 to 5 halogen atoms, with the proviso that $R^{31}$ and $R^{33}$ each do not represent fluorine if $R^1$ represents trifluoromethyl and $R^2$ represents hydrogen.

Very particularly preferred are biphenylbenzamide derivatives of the formulae (Ic), (Id) and (Ie), in which in each case $R^1$ represents trifluoromethyl or iodine,
$R^2$ represents hydrogen,
$R^{31}$, $R^{32}$ and $R^{33}$ independently of one another represent fluorine, chlorine, bromine, methyl, methoxy, methylthio, trifluoromethyl, trifluoromethoxy or trifluoromethylthio, with the proviso that $R^{31}$ and $R^{33}$ each do not represent fluorine if $R^1$ represents trifluoromethyl and $R^2$ represents hydrogen.

Furthermore, it has been found that the novel biphenylbenzamide derivatives of the formulae (Ia), (Ib), (Ic), (Id) and (Ie) have very good microbicidal properties and can be used both in crop protection and in the protection of materials for controlling unwanted microorganisms.

The general or preferred radical definitions or illustrations given above can also be combined with one another as desired, i.e. including combinations between the respective ranges and preferred ranges. The definitions apply both to the end products and, correspondingly, to precursors and intermediates. Moreover, individual definitions may not apply.

Saturated hydrocarbon radicals, such as alkyl, can in each case be straight-chain or branched as far as this is possible, including in combination with heteroatoms, such as, for example, in alkoxy.

Halogen-substituted radicals, for example haloalkyl, are mono- or polyhalogenated up to the maximum possible number of substituents. In the case of polyhalogenation, the halogen atoms can be identical or different. Here, halogen represents fluorine, chlorine, bromine or iodine, in particular fluorine, chlorine or bromine.

Biphenylbenzamide derivatives of the formulae (Ia), (Ib), (Ic), (Id) and (Ie) are in each case sub-groups of the compounds of the formula (I) which can be used according to the invention. In principle, these compounds can be prepared by the same route. Accordingly, the preparation of the compounds of the formula (I) is described hereinbelow by way of example.

Compounds of the formula (I) can be prepared by

A) reacting benzoyl halides of the formula (II)

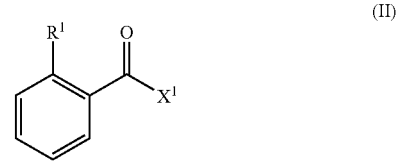

in which
$R^1$ is as defined above,
$X^1$ represents halogen,
with aniline derivatives of the formula (III)

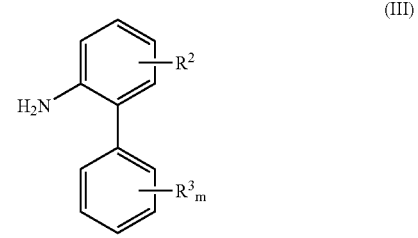

in which
$R^2$, $R^3$ and m are as defined above,
if appropriate in the presence of an acid binder and if appropriate in the presence of a diluent, or B) reacting halobenzainides of the formula (IV)

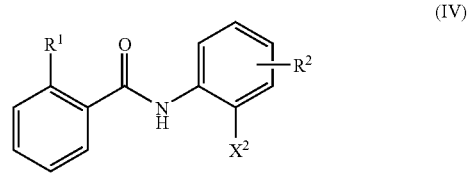

in which
$R^1$ and $R^2$ are as defined above,
$X^2$ represents bromine or iodine,
with boronic acid derivatives of the formula (V)

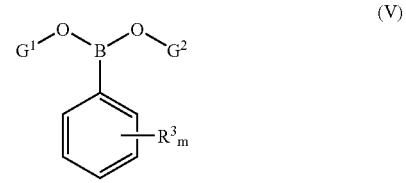

in which
$R^3$ and m are as defined above,
$G^1$ and $G^2$ each represent hydrogen or together represent tetramethylethylene in the presence of a catalyst, if appropriate in the presence of an acid binder and if appropriate in the presence of a diluent, or C) reacting benzamide boronic acid derivatives of the formula (VI)

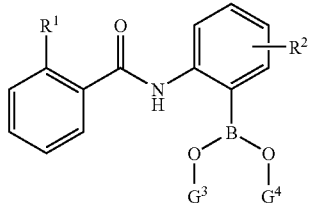

(VI)

in which
R¹ and R² are as defined above,
G³ and G⁴ each represent hydrogen or together represent tetramethylethylene
with halobenzene derivatives of the formula (VII)

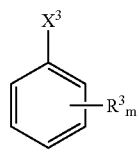

(VII)

in which
R³ and m are as defined above and
X³ represents bromine, iodine or trifluoromethylsulphonyloxy,
in the presence of a catalyst, if appropriate in the presence of an acid binder and if appropriate in the presence of a diluent, or D) reacting halobenzamides of the formula (IV)

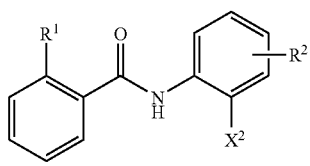

(IV)

in which
R¹ and R² are as defined above,
X² represents bromine or iodine,
in a first step with a diborane derivative of the formula (VIII)

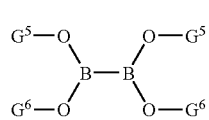

(VIII)

in which
G⁵ and G⁶ each represent alkyl or together represent alkanediyl, in the presence of a catalyst, if appropriate in the presence of an acid binder and if appropriate in the presence of a diluent and, without work-up, in a second step with halobenzene derivatives of the formula (VII)

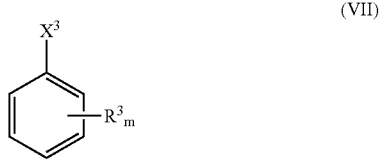

(VII)

in which
R³ and m are as defined above and
X³ represents bromine, iodine or trifluoromethylsulphonyloxy,
in the presence of a catalyst, if appropriate in the presence of an acid binder and if appropriate in the presence of a diluent.

Using, for example, 2-(trifluoromethyl)benzoyl chloride and 4'-chloro-1,1'-biphenyl-2-amine as starting materials and a base, the course of the process A) according to the invention can be illustrated by the following equation:

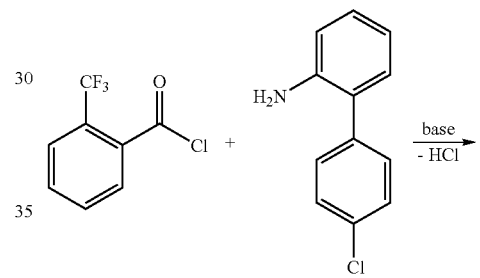

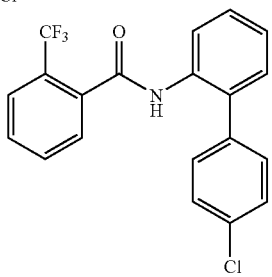

The formula (II) provides a general definition of the benzoyl halides required as starting materials for carrying out the process A) according to the invention. In this formula (II), R¹ preferably, particularly preferably and very particularly preferably has those meanings which have already been mentioned in connection with the description of the compounds of the formula (I) which can be used according to the invention as being preferred, particularly preferred, etc., for this radical. X¹ preferably represents chlorine.

The benzoyl halides of the formula (II) are known and/or can be prepared by known processes (compare, for example EP-A 0 276 177).

The formula (III) provides a general definition of the aniline derivatives furthermore required as starting materials for carrying out the process A) according to the invention. In this formula (III), R², R³ and m preferably, particularly preferably and very particularly preferably have those meanings which have already been mentioned in connection with the description of the compounds of the formula (I) which can be used according to the invention as being preferred, particularly preferred, etc., for these radicals.

The aniline derivatives of the formula (III) are known and/or can be prepared by known methods (cf., for example, Bull. Korean Chem. Soc. 2000 21, 165–166; Chem. Pharm. Bull. 1992, 40, 240–4; JP 9132567).

Using, for example, N-(2-iodophenyl)-2-(trifluoromethyl)benzamide and 4-chlorophenylboronic acid as starting materials and a catalyst and a base, the course of the process B) according to the invention can be illustrated by the following equation:

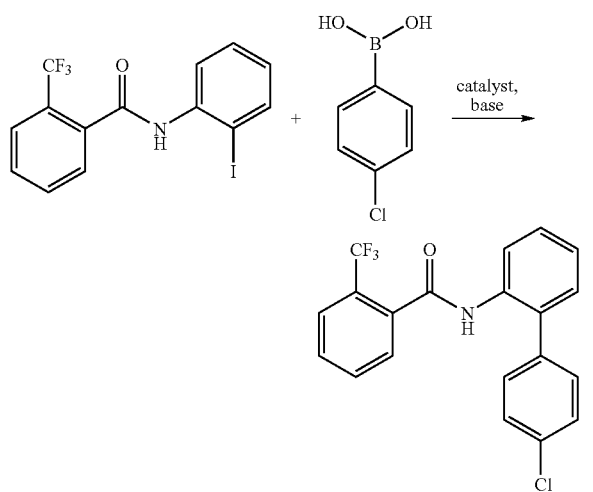

The formula (IV) provides a general definition of the halobenzamides required as starting materials for carrying out the process B) according to the invention. In this formula (IV), $R^1$ and $R^2$ preferably, particularly preferably and very particularly preferably have those meanings which have already been mentioned in connection with the description of the compounds of the formula (I) which can be used according to the invention as being preferred, particularly preferred, etc., for these radicals. $X^2$ preferably represents bromine or iodine.

The halobenzamides of the formula (IV) have hitherto not been disclosed. They are novel chemical compounds and also form part of the subject-matter of the present application. They are obtained by E) reacting benzoyl halides of the formula (II)

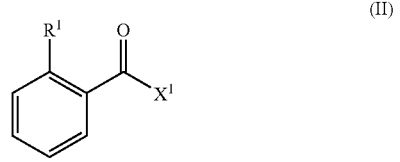

in which
$R^1$ is as defined above,
$X^1$ represents halogen,
with 2-bromoaniline or 2-iodoaniline.

The benzoyl halides of the formula (II) required as starting materials for carrying out the process E) according to the invention have already been described further above, in connection with process A) according to the invention.

The compounds 2-bromoaniline and 2-iodoaniline furthermore required as starting materials for carrying out the process E) according to the invention are known chemicals for synthesis.

The formula (V) provides a general definition of the boronic acid derivatives furthermore required as starting materials for carrying out the process B) according to the invention. In this formula (V), $R^3$ and m preferably, particularly preferably and very particularly preferably have those meanings which have already been mentioned in connection with the description of the compounds of the formula (I) which can be used according to the invention as being preferred, particularly preferred, etc., for these radicals. $G^1$ and $G^2$ preferably each represent hydrogen or together represent tetramethylethylene.

Boronic acid derivatives of the formula (V) are known chemicals for synthesis. They can also be prepared directly, immediately prior to the reaction, from halobenzene derivatives and boronic acid esters, and reacted further without any work-up.

Using, for example, N-[2-(4,4,5,5-tetramethyl-1,3,2-dioxaborolan-2-yl)phenyl]-2-(trifluoromethyl)benzamide and 4-chlorophenyltrifluoromethanesulphonic acid as starting materials and a catalyst and a base, the course for the process C) according to the invention can be illustrated by the following equation:

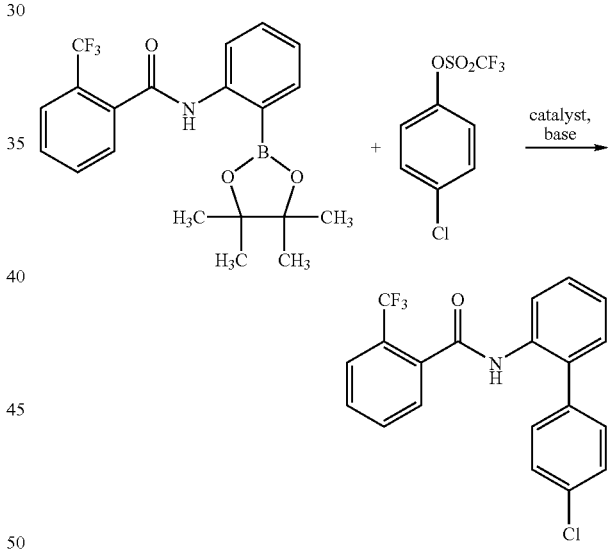

The formula (VI) provides a general definition of the benzamide boronic acid derivatives required as starting materials for carrying out the process C) according to the invention. In this formula (VI), $R^1$ and $R^2$ preferably, particularly preferably and very particularly preferably have those meanings which have already been mentioned in connection with the description of compounds of the formula (I) which c an b e used according to the invention as being preferred, particularly preferred, etc., for these radicals. $G^3$ and $G^4$ preferably each represent hydrogen or together represent tetramethylethylene.

The benzamide boronic acid derivatives of the formula (VI) have hitherto not been disclosed. They are novel chemical compounds and also form part of the subject-matter of the present application.

They are obtained by

F) reacting benzoyl halides of the formula (II)

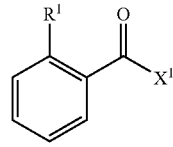

in which
R$^1$ is as defined above,
X$^1$ represents halogen,
with aniline boronic derivatives of the formula (IX)

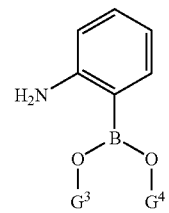

in which
G$^3$ and G$^4$ are as defined above,
if appropriate in the presence of an acid binder and if appropriate in the presence of a diluent.

The benzoyl halides of the formula (II) required as starting materials for carrying out the process F) according to the invention have already been described above in connection with the process A) according to the invention.

The formula (IX) provides a general definition of the anilineboronic acid derivatives furthermore required as starting materials for carrying out the process F) according to the invention. In this formula (IX), G$^3$ and G$^4$ preferably each represent hydrogen or together represent tetramethylethylene.

The anilineboronic acid derivatives of the formula (IX) required as starting materials for carrying out the process F) according to the invention are known chemicals for synthesis.

The formula (VII) provides a general definition of the halobenzene derivatives furthermore required as starting materials for carrying out the process C) according to the invention. In this formula (VII), R$^3$ and m preferably, particularly preferably and very particularly preferably have those meanings which have already been mentioned in connection with the description of the compounds of the formula (I) which can be used according to the invention as being preferred, particularly preferred, etc., for these radicals. X$^3$ preferably represents bromine, iodine or trifluoromethylsulphonyloxy.

Using, for example, N-(2-bromophenyl)-2-(trifluoromethyl)benzamide and 4,4,4',4',5,5,5',5'-octamethyl-2,2'-bis-1,3,2-dioxaborolane in the first step and furthermore 4-bromo-1-chloro-2-methylbenzene in the second step as starting materials and in each step a catalyst and a base, the course of the process D) according to the invention can be illustrated by the following equation:

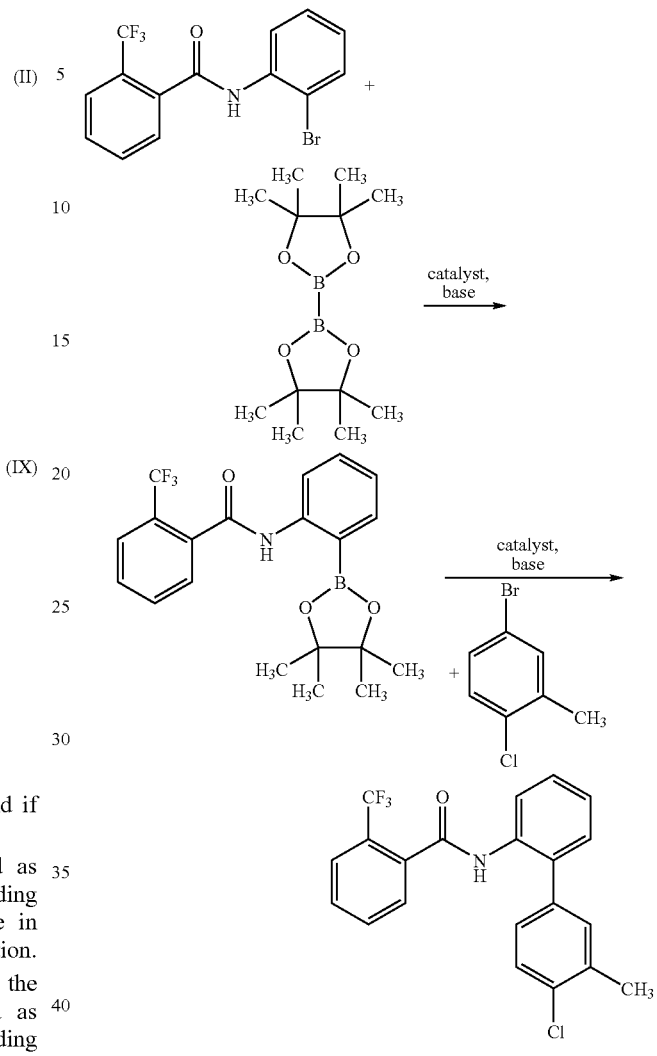

The halobenzamides of the formula (IV) required as starting materials for carrying out the process D) according to the invention have already been described above in connection with process B) according to the invention.

The formula (VIII) provides a general definition of the diborane derivatives furthermore required as starting materials for carrying out the process D) according to the invention. In this formula (VIII), G$^5$ and G$^6$ preferably each represent methyl, ethyl, propyl, butyl or together represent tetramethylethylene.

The diborane derivatives of the formula (VIII) are generally known chemicals for synthesis.

The halobenzene derivatives of the formula (VII) furthermore required as starting materials for carrying out the process D) according to the invention have already been described above, in connection with the process C) according to the invention.

Suitable diluents for carrying out the processes A), E) and F) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole, or amides, such as N,N-dimethylformamide, N,N-dimethylacetamide, N-methylformanilide, N-methylpyrrolidone or hexamethylphosphoric triamide.

The processes A), E) and F) according to the invention are, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or caesium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethyl-aminopyridine, diazabicyclooctane (DABCO), diazabicyclononene (DBN) or diazabicycloundecene (DBU).

When carrying out the processes A), E) and F) according to the invention, the reaction temperatures can be varied within a relatively wide range. In general, the processes are carried out at temperatures of from 0° C. to 150° C., preferably at temperatures of from 20° C. to 110° C.

For carrying out the process A) according to the invention for preparing the compounds of the formula (I), in general from 0.2 to 5 mol, preferably from 0.5 to 2 mol, of the aniline derivative of the formula (III) are employed per mole of the benzoyl halide of the formula (II). Work-up is carried out by customary methods.

For carrying out the process E) according to the invention for preparing compounds of the formula (III), in general from 0.2 to 5 mol, preferably from 0.5 to 2 mol, of 2-bromoaniline or 2-iodoaniline are employed per mole of the benzoyl halide of the formula (II). Work-up is carried out by customary methods.

For carrying out the process F) according to the invention for preparing the compounds of the formula (VI), in general from 0.2 to 5 mol, preferably from 0.5 to 2 mol, of the aniline boronic acid derivative of the formula (IX) are employed per mole of the benzoyl halide of the formula (II). Work-up is carried out by customary methods.

Suitable diluents for carrying out the processes B), C) and D) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methyl-pyrrolidone or hexamethylphosphoric triamide; esters, such methyl acetate or ethyl acetate; sulphoxides, such as dimethyl sulphoxide; sulphones, such as sulpholane; alcohols, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, mixtures thereof with water or pure water.

When carrying out the processes B), C) and D) according to the invention, the reaction temperatures can be varied within a relatively wide range. In general, the processes are carried out at temperatures of from 0° C. to 150° C., preferably at temperatures of from 20° C. to 110° C.

The processes B), C) and D) according to the invention are, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, fluorides, phosphates, carbonates or bicarbonates, such as, for example, sodium hydride, sodium amide, lithium diisopropylamide, sodium methoxide, sodium ethoxide, potassium tert-butoxide, sodium hydroxide, potassium hydroxide, sodium acetate, sodium phosphate, potassium phosphate, potassium fluoride, caesium fluoride, sodium carbonate, potassium carbonate, potassium bicarbonate, sodium bicarbonate or caesium carbonate, and also tertiary amines, such as trimethylamine, triethylamine, tributylamine, N,N-dimethylaniline, N,N-dimethylbenzylamine, pyridine, N-methyl-piperidine, N-methylmorpholine, N,N-dimethylaminopyridine, diazabicyclooctane (DABCO), diazabicyclononene (DBN) or diazabicycloundecene (DBU).

The processes B), C) and D) according to the invention are carried out in the presence of a catalyst, such as, for example, a palladium salt or complex. Preferably used for this purpose are palladium chloride, palladium acetate, tetrakis(triphenyl-phosphine)palladium, bis(triphenylphosphine)palladium dichloride or (1,1'-bis(diphenylphosphino) ferrocenepalladium(II) chloride).

It is also possible to generate a palladium complex in the reaction mixture by separate addition of a palladium salt and a complex ligand, such as, for example, triethyl-phosphine, tri-tert-butylphosphine, tricyclohexylphosphine, 2-(dicyclohexyl-phosphine)biphenyl, 2-(di-tert-butylphosphine)biphenyl, 2-(dicyclohexylphosphine)-2'-(N,N-dimethylamino)biphenyl, triphenylphosphine, tris-(o-tolyl)phosphine, sodium 3-(diphenylphosphino)benzenesulphonate, tris-2-(methoxyphenyl)-phosphine, 2,2'-bis(diphenylphosphine)-1,1'-binaphthyl, 1,4-bis(diphenylphosphine)-butane, 1,2-bis (diphenylphosphine)ethane, 1,4-bis (dicyclohexylphosphine)butane, 1,2-bis (dicyclohexylphosphine)ethane, 2-(dicyclohexylphosphine)-2'-(N,N-dimethyl-amino)biphenyl, bis(diphenylphosphino)ferrocene or tris-(2,4-tert-butylphenyl)phosphite to the reaction.

For carrying out the process B) according to the invention for preparing the compounds of the formula (I), in general from 1 to 15 mol, preferably from 2 to 8 mol, of the boronic acid derivative of the formula (V) are employed per mole of the halobenzamide of the formula (IV). Work-up is carried out by customary methods.

For carrying out the process C) according to the invention for preparing the compounds of the formula (I), in general from 1 to 15 mol, preferably from 2 to 8 mol, of halobenzene derivative of the formula (VII) are employed per mole of the benzamide boronic acid derivative of the formula (VI). Work-up is carried out by customary methods.

For carrying out the process D) according to the invention for preparing the compounds of the formula (I), in general from 1 to 15 mol, preferably from 1 to 5 mol, of diborane derivative of the formula (VIII) and from 1 to 15 mol, preferably from 1 to 5 mol, of halobenzene derivative of the formula (VII) are employed per mole of the halobenzene derivative of the formula (IV).

The processes A), B), C), D), E) and F) according to the invention are generally carried out under atmospheric pressure. However, it is also possible to operate under elevated or reduced pressure—in general between 0.1 bar and 10 bar.

The active compounds of the formulae (Ia), (Ib), (Ic), (Id) and (Ie) according to the invention have potent microbicidal activity and can be employed for controlling undesirable microorganisms, such as fungi and bacteria, in crop protection and in the protection of materials.

Fungicides can be employed in crop protection for controlling *Plasmodiophoromycetes, Oomycetes, Chytridiomycetes, Zygomycetes, Ascomycetes, Basidiomycetes* and *Deuteromycetes*.

Bactericides can be employed in crop protection for controlling *Pseudomonadaceae, Rhizobiaceae, Enterobacteriaceae, Corynebacteriaceae* and *Streptomycetaceae*.

Some pathogens causing fungal and bacterial diseases which come under the generic names listed above may be mentioned as examples, but not by way of limitation:

Xanthomonas species, such as, for example, *Xanthomonas campestris* pv. *oryzae*;
Pseudomonas species, such as, for example, *Pseudomonas syringae* pv. *lachrymans*;
Erwinia species, such as, for example, *Erwinia amylovora*;
Pythium species, such as, for example, *Pythium ultimum*;
Phytophthora species, such as, for example, *Phytophthora infestans*;
Pseudoperonospora species, such as, for example, *Pseudoperonospora humuli* or *Pseudoperonospora cubensis*;
Plasmopara species, such as, for example, *Plasmopara viticola*;
Bremia species, such as, for example, *Bremia lactucae*;
Peronospora species, such as, for example, *Peronospora pisi* or *P. brassicae*;
Erysiphe species, such as, for example, *Erysiphe graminis*;
Sphaerotheca species, such as, for example, *Sphaerotheca fuliginea*;
Podosphaera species, such as, for example, *Podosphaera leucotricha*;
Venturia species, such as, for example, *Venturia inaequalis*;
Pyrenophora species, such as, for example, *Pyrenophora teres* or *P. graminea* (conidia form: *Drechslera*, syn: *Helminthosporium*);
Cochliobolus species, such as, for example, *Cochliobolus sativus* (conidia form: *Drechslera*, syn: *Helminthosporium*);
Uromyces species, such as, for example, *Uromyces appendiculatus*;
Puccinia species, such as, for example, *Puccinia recondita*;
Sclerotinia species, such as, for example, *Sclerotinia sclerotiorum*;
Tilletia species, such as, for example, *Tilletia caries*;
Ustilago species, such as, for example, *Ustilago nuda* or *Ustilago avenae*;
Pellicularia species, such as, for example, *Pellicularia sasakii*;
Pyricularia species, such as, for example, *Pyricularia oryzae*;
Fusarium species, such as, for example, *Fusarium culmorum*;
Botrytis species, such as, for example, *Botrytis cinerea*;
Uncinula species, such as, for example, *Uncinula necator*;
Septoria species, such as, for example, *Septoria nodorum*;
Leptosphaeria species, such as, for example, *Leptosphaeria nodorum*;
Cercospora species, such as, for example, *Cercospora canescens*;
Alternaria species, such as, for example, *Alternaria brassicae*; and
Pseudocercosporella species, such as, for example, *Pseudocercosporella herpotrichoides*.

The active compounds of the formulae (Ia), (Ib), (Ic), (Id) and (Ie) according to the invention also show a strong invigorating action in plants. Accordingly, they are suitable for mobilizing the internal defences of the plant against attack by unwanted microorganisms.

In the present context, plant-invigorating (resistance-inducing) compounds are to be understood as meaning substances which are capable of stimulating the defence system of plants such that, when the treated plants are subsequently inoculated with unwanted microorganisms, they display substantial resistance to these microorganisms.

In the present case, unwanted microorganisms are to be understood as meaning phytopathogenic fungi, bacteria and viruses. The compounds according to the invention can thus be used to protect plants within a certain period of time after treatment against attack by the pathogens mentioned. The period of time for which this protection is achieved generally extends for 1 to 10 days, preferably 1 to 7 days, from the treatment of the plants with the active compounds.

The fact that the active compounds are well tolerated by plants at the concentrations required for controlling plant diseases permits the treatment of above-ground parts of plants, of propagation stock and seeds, and of the soil.

The active compounds of the formulae (Ia), (Ib), (Ic), (Id) and (Ie) according to the invention are also suitable for increasing the yield of crops. In addition, they show reduced toxicity and are well tolerated by plants.

If appropriate, the active compounds of the formulae (Ia), (Ib), (Ic), (Id) and (Ie) according to the invention can, at certain concentrations and application rates, also be employed as herbicides, for regulating plant growth and for controlling animal pests. If appropriate, they can also be used as intermediates or precursors in the synthesis of other active compounds.

According to the invention, it is possible to treat all plants and parts of plants. Plants are to be understood here as meaning all plants and plant populations, such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested material and vegetative and generative propagation material, for example seedlings, tubers, rhizomes, cuttings and seeds.

The treatment of the plants and parts of plants according to the invention with the active compounds of the formulae (Ia), (Ib), (Ic), (Id) and (Ie) is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

In the protection of materials, the compounds of the formulae (Ia), (Ib), (Ic), (Id) and (Ie) according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be tackifiers, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably tackifiers, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes) and against slime organisms and algae.

Microorganisms of the following genera may be mentioned as examples:
Alternaria, such as Alternaria tenuis,
Aspergillus, such as Aspergillus niger,
Chaetomium, such as Chaetomium globosum,
Coniophora, such as Coniophora puetana,
Lentinus, such as Lentinus tigrinus,
Penicillium, such as Penicillium glaucum,
Polyporus, such as Polyporus versicolor,
Aureobasidium, such as Aureobasidium pullulans,
Sclerophoma, such as Sclerophoma pityophila,
Trichoderma, such as Trichoderma viride,
Escherichia, such as Escherichia coli,
Pseudomonas, such as Pseudomonas aeruginosa, and
Staphylococcus, such as Staphylococcus aureus.

Depending on their particular physical and/or chemical properties, the active compounds can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide.

Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention can, as such or in their formulations, also be used in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Suitable mixing components are, for example, the following compounds:

Fungicides:
2-phenylphenol; 8-hydroxyquinoline sulphate;
acibenzolar-S-methyl; aldimorph; amidoflumet; ampropylfos; ampropylfos-potassium;
andoprim; anilazine; azaconazole; azoxystrobin;
benalaxyl; benodanil; benomyl; benthiavalicarb-isopropyl; benzamacril; benzamacril-isobutyl;
bilanafos; binapacryl; biphenyl; bitertanol; blasticidin-S; bromuconazole;
bupirimate; buthiobate; butylamine;
calcium polysulphide; capsimycin; captafol; captan; carbendazim; carboxin;
carpropamid; carvone; chinomethionat; chlobenthiazone; chlorfenazole; chloroneb;
chlorothalonil; chlozolinate; clozylacon; cyazofamid; cyflufenamid; cymoxanil;
cyproconazole; cyprodinil; cyprofuram;
Dagger G; debacarb; dichlofluanid; dichlone; dichlorophen; diclocymet; diclomezine;
dicloran; diethofencarb; difenoconazole; diflumetorim; dimethirimol;

dimethomorph; dimoxystrobin; diniconazole; diniconazole-M; dinocap; diphenylamine;

dipyrithione; ditalimfos; dithianon; dodine; drazoxolon;

edifenphos; epoxiconazole; ethaboxam; ethirimol; etridiazole;

famoxadone; fenamidone; fenapanil; fenarimol; fenbuconazole; fenfuram; fenhexamid;

fenitropan; fenoxanil; fenpiclonil; fenpropidin; fenpropimorph; ferbam;

fluazinam; flubenzinine; fludioxonil; flumetover; flumorph; fluoromide;

fluoxastrobin; fluquinconazole; flurprimidol; flusilazole; flusulfamide; flutolanil;

flutriafol; folpet; fosetyl-Al; fosetyl-sodium; fuberidazole; furalaxyl; furametpyr;

furcarbanil; furmecyclox;

guazatine; hexachlorobenzene; hexaconazole; hymexazole;

imazalil; imibenconazole; iminoctadine triacetate; iminoctadine tris(albesil);

iodocarb; ipconazole; iprobenfos; iprodione; iprovalicarb; irumamycin;

isoprothiolane; isovaledione;

kasugamycin; kresoxim-methyl;

mancozeb; maneb; meferimzone; mepanipyrim; mepronil; metalaxyl; metalaxyl-M;

metconazole; methasulfocarb; methfuroxam; metiram; metominostrobin; metsulfovax;

mildiomycin; myclobutanil; myclozolin;

natamycin; nicobifen; nitrothal-isopropyl; noviflumuron; nuarimol;

ofurace; orysastrobin; oxadixyl; oxolinic acid; oxpoconazole; oxycarboxin;

oxyfenthiin;

paclobutrazole; pefurazoate; penconazole; pencycuron; phosdiphen; phthalide; picoxystrobin;

piperalin; polyoxins; polyoxorim; probenazole; prochloraz; procymidone;

propamocarb; propanosine-sodium; propiconazole; propineb; proquinazid; prothioconazole;

pyraclostrobin; pyrazophos; pyrifenox; pyrimethanil; pyroquilon;

pyroxyfur; pyrrolenitrine;

quinconazole; quinoxyfen; quintozene;

simeconazole; spiroxamine; sulphur;

tebuconazole; tecloftalam; tecnazene; tetcyclacis; tetraconazole; thiabendazole;

thicyofen; thifluzamide; thiophanate-methyl; thiram; tioxymid; tolclofos-methyl;

tolylfluanid; triadimefon; triadimenol; triazbutil; triazoxide; tricyclamide; tricyclazole;

tridemorph; trifloxystrobin; triflumizole; triforine; triticonazole;

uniconazole; validamycin A; vinclozolin;

zineb; ziram; zoxamide;

(2S)-N-[2-[4-[[3-(4-chlorophenyl)-2-propynyl]oxy]-3-methoxyphenyl]ethyl]-3-methyl-2-[(methylsulphonyl)amino]butanamide; 1-(1-naphthalenyl)-1H-pyrrole-2,5-dione; 2,3,5,6-tetrachloro-4-(methylsulphonyl)pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; actinovate; cis-1-(4-chlorophenyl)-2-(1H-1,2,4-triazol-1-yl)cycloheptanol; methyl 1-(2,3-dihydro-2,2-dimethyl-1H-inden-1-yl)-1H-imidazole-5-carboxylate; monopotassium carbonate; N-(6-methoxy-3-pyridinyl)cyclopropanecarboxamide; N-butyl-8-(1,1-dimethylethyl)-1-oxaspiro[4.5]decane-3-amine; sodium tetrathiocarbonate;

and copper salts and preparations, such as Bordeaux mixture; copper hydroxide;

copper naphthenate; copper oxychloride; copper sulphate; cufraneb; copper oxide; mancopper; oxine-copper.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/acaricides/nematicides:

abanectin, ABG-9008, acephate, acequinocyl, acetamiprid, acetoprole, acrinathrin, AKD-1022, AKD-3059, AKD-3088, alanycarb, aldicarb, aldoxycarb, allethrin, allethrin 1R-isomers, alpha-cypermethrin (alphamethrin), amidoflumet, aminocarb, amitraz, avermectin, AZ-60541, azadirachtin, azamethiphos, azinphos-methyl, azinphos-ethyl, azocyclotin,

*Bacillus popilliae, Bacillus sphaericus, Bacillus subtilis, Bacillus thuringiensis, Bacillus thuringiensis* strain EG-2348, *Bacillus thuringiensis* strain GC-91, *Bacillus thuringiensis* strain NCTC-11821, Obaculoviruses, Beauveria bassiana, Beauveria tenella, bendiocarb, benfuracarb, bensultap, benzoximate, beta-cyfluthrin, beta-cypermethrin, bifenazate, bifenthrin, binapacryl, bioallethrin, bioallethrin-S-cyclopentyl-isomer, bioethanomethrin, biopermethrin, bioresmethrin, bistrifluron, BPMC, brofen-prox, bromophos-ethyl, bromopropylate, bromfenvinfos (-methyl), BTG-504, BTG-505, bufencarb, buprofezin, butathiofos, butocarboxim, butoxycarboxim, butylpyridaben, cadusafos, camphechlor, carbaryl, carbofuran, carbophenothion, carbosulfan, cartap, CGA-50439, chinomethionat, chlordane, chlordimeform, chloethocarb, chlorethoxyfos, chlorfenapyr, chlorfenvinphos, chlorfluazuron, chlonnephos, chlorobenzilate, chloropicrin, chlorproxyfen, chlorpyrifos-methyl, chlorpyrifos (-ethyl), chlovaporthrin, chromafenozide, cis-cypermethrin, cis-resmethrin, cis-permethrin, clocythrin, cloethocarb, clofentezine, clothianidin, clothiazoben, codlemone, coumaphos, cyanofenphos, cyanophos, cycloprene, cycloprothrin, Cydia pomonella, cyfluthrin, cyhalothrin, cyhexatin, cypennethrin, cyphenothrin (1R-trans-isomer), cyromazine, DDT, deltamethrin, demeton-S-methyl, demeton-S-methylsulphone, diafenthiuron, dialifos, diazinon, dichlofenthion, dichlorvos, dicofol, dicrotophos, dicyclanil, diflubenzuron, dimethoate, dimethylvinphos, dinobuton, dinocap, dinotefuran, diofenolan, disulfoton, docusat-sodium, dofenapyn, DOWCO-439, eflusilanate, emamectin, emamectin-benzoate, empenthrin (1R-isomer), endosulfan, *Entomopthora* spp., EPN, esfenvalerate, ethiofencarb, ethiprole, ethion, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulfothion, fenthion, fentrifanil, fenvalerate, fipronil, flonicamid, fluacrypyrim, fluazuron, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), fuirathiocarb, gamma-HCH, gossyplure, grandlure, granulosis viruses, halfenprox, halofenozide, HCH, HCN-801, heptenophos, hexaflumuron, hexythiazox, hydramethylnone, hydroprene, IKA-2002, imidacloprid, imiprothrin, indoxacarb, iodofenphos, iprobenfos, isazofos, isofenphos, isoprocarb, isoxathion, ivermectin, japonilure, kadethrin, nuclear polyhedrosis viruses, kinoprene, lambda-cyhalothrin, lindane, lufenuron, malathion, mecarbam, mesulfenfos, metaldehyde, metam-sodium, methacrifos, methamidophos, Metharhizium anisopliae, Metharhizium flavoviride, methidathion, methiocarb, methomyl, methoprene, methoxychlor, methoxyfenozide, metolcarb, metoxadiazone, mevinphos, milbemectin, milbemycin, MKI-245, MON-45700, monocrotophos, moxidectin, MTI-800, naled, NC-104, NC-170, NC-184, NC-194, NC-196, niclosamide, nicotine, nitenpyram, nithiazine, NNI-0001, NNI-0101, NNI-0250, NNI-9768, novaluron, novi-flumuron, OK-5101, OK-5201, OK-9601, OK-9602, OK-9701, OK-9802, omethoate, oxamyl, oxydemeton-methyl,

*Paecilomyces* fuimosoroseus, parathion-methyl, parathion (-ethyl), permethrin (cis-, trans-), petroleum, PH-6045, phenothrin (1R-trans isomer), phenthoate, phorate, phosalone, phosmet, phosphamidon, phosphocarb, phoxim, piperonyl butoxide, pirimicarb, pirimiphos-methyl, pirimiphos-ethyl, prallethrin, profenofos, promecarb, propaphos, propargite, propetamphos, propoxur, prothiofos, prothoate, protrifenbute, pymetrozine, pyraclofos, pyresmethrin, pyrethrum, pyridaben, pyridalyl, pyridaphenthion, pyridathion, pyrimidifen, pyriproxyfen, quinalphos, resmethrin, RH-5849, ribavirin, RU-12457, RU-15525, S-421, S-1833, salithion, sebufos, SI-0009, silafluofen, spinosad, spirodiclofen, spiromesifen, sulfluramid, sulfotep, sulprofos, SZI-121, tau-fluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (lR-isomer), tetrasul, theta-cypermethrin, thiacloprid, thiamethoxam, thiapronil, thiatriphos, thiocyclam hydrogenoxalate, thiodicarb, thiofanox, thiometon, thiosultap-sodium, thuringiensin, tolfenpyrad, tralocythrin, tralomethrin, transfluthrin, triarathene, triazamate, triazophos, triazuron, trichlophenidine, trichlorfon, triflumuron, trimethacarb, vamidothion, vaniliprole, verbutin, Verticillium lecanii,

WL-108477, WL-40027,

YI-5201, YI-5301, YI-5302,

XMC, xylylcarb,

ZA-3274, zeta-cypermethrin, zolaprofos, ZXI-8901, the compound 3-methylphenyl propylcarbamate (tsumacide Z), the compound 3-(5-chloro-3-pyridinyl)-8-(2,2,2-trifluoroethyl)-8-azabicyclo[3.2.1]-octane-3-carbonitrile (CAS-Reg. No. 185982-80-3) and the corresponding 3-endo-isomer (CAS-Reg. No. 185984-60-5) (cf. WO-96/37494, WO-98/25923), and preparations which comprise insecticidally active plant extracts, nematodes, fungi or viruses.

A mixture with other known active compounds, such as herbicides, or with fertilizers and growth regulators, safeners and/or semiochemicals is also possible.

In addition, the compounds of the formula (I) according to the invention also have very good antimycotic activity. They have a very broad antimycotic activity spectrum in particular against dermatophytes and yeasts, moulds and diphasic fungi (for example against *Candida* species such as *Candida albicans, Candida glabrata*) and *Epidermophyton floccosum, Aspergillus* species such as *Aspergillus niger* and *Aspergillus fumigatus, Trichophyton* species such as *Trichophyton mentagrophytes, Microsporon* species such as *Microsporon canis* and *audouinii*. The list of these fungi does by no means limit the mycotic spectrum which can be covered, but is only for illustration.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10,000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10,000 g/ha, preferably between 1 and 5000 g/ha.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, varieties, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized are in particular increased defence of the plants against insects by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants").

Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucoton® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars having these genetic traits or genetic traits still to be developed, which plants will be developed and/or marketed in the future.

The plants listed can be treated according to the invention in a particularly advantageous manner with the compounds of the general formulae (I), (Ia), (Ib), (Ic), (Id) and (Ie) or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The preparation and the use of the active compounds according to the invention is illustrated by the examples below.

PREPARATION EXAMPLES

Example 1

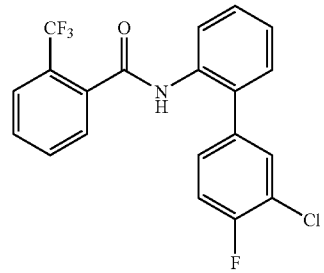

Process A):

0.288 g (1.3 mmol) of 3'-chloro-4'-fluoro-1,1'-biphenyl-2-amine is dissolved in 3 ml of tetrahydrofuran and 0.36 ml (2.6 mmol) of triethylamine and 0.25 g (1.56 mmol) of 2-trifluoromethylbenzoyl chloride (dissolved in 3 ml of tetrahydrofuran) are added. The reaction solution is stirred at 60° C. for 16 h. For work-up, the mixture is concentrated and the crude product is purified by column chromatography (cyclohexane/ethyl acetate 2:1).

This gives 0.491 g (96% of theory) of N-(3'-chloro-4'-fluoro-1,1'-biphenyl-2-yl)-2-(trifluoromethyl)benzamide (compound 35, cf. Table 1) of logP (pH 2.3)=3.81.

Example 2

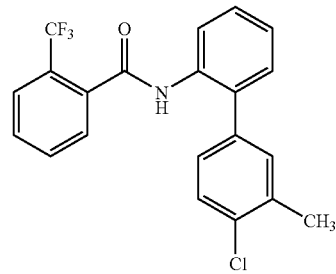

Process D)

226 mg (1.1 mmol) of 2-chloro-5-bromotoluene, 245 mg (2.5 mmol) of potassium acetate and 279 m g (1.1 m mol) of pinacoldiboronic ester are dissolved in 8 ml of dimethylformamide (which contains as little oxygen as possible), and a catalytic amount (0.1 eq.) of PdCl$_2$(dppf) is added. The reaction mixture is stirred at 80–90° C. for 2 h and, after cooling, 5 eq. of 2 M sodium carbonate solution, 344 mg (1.0 mmol) of N-(2-bromophenyl)-2-(trifluoromethyl)benzamide (dissolved in 4 ml of dimethylformamide) and a further 0.1 eq. of catalyst are added. The reaction solution is stirred at 80–90° C. for 16 h. For work-up, 2 ml of water and 8 ml of ethyl acetate are added. The organic phase is concentrated and purified by column chromatography (cyclohexane/ethyl acetate 1:1).

This gives 151 mg (39% of theory) of N-(4'-chloro-3'-methyl-1,1'-biphenyl-2-yl)-2-(trifluoromethyl)benzamide (compound 42, cf. Table 1) of logP (pH 2.3)=4.18.

The compounds of the formula (I) listed in Table 1 below can be obtained analogously to Examples 1 and 2 and in accordance with the general descriptions of the processes A) to D) according to the invention. The last column of the table states to which group of novel compounds according to the invention the substance in question belongs.

TABLE 1

(I)

| No. | R$^1$ | R$^2$ | m | R$^3$ | logP (pH 2.3) | Group |
|---|---|---|---|---|---|---|
| 1 | CF$_3$ | H | 1 | 4-Cl | 3.73 | 3 |
| 2 | CF$_3$ | H | 2 | 2,4-Cl$_2$ | 4.00 | 1 |
| 3 | CF$_3$ | H | 2 | 2-CH$_3$, 4-Cl | 4.14 | 1 |
| 4 | CF$_3$ | H | 2 | 3,4-Cl$_2$ | 4.13 | 1 |
| 5 | CF$_3$ | H | 1 | 4-Br | 4.03 | 3 |
| 6 | CF$_3$ | H | 1 | 4-CF$_3$ | 4.05 | 3 |
| 7 | CF$_3$ | H | 1 | 3-Cl | 3.86 | 4 |
| 8 | CF$_3$ | H | 1 | 4-OCF$_3$ | 4.20 | 3 |
| 9 | CF$_3$ | H | 1 | 4-SCH$_3$ | 3.89 | 3 |
| 10 | Cl | H | 1 | 4-Br | 3.89 | 3 |
| 11 | Cl | H | 1 | 4-CF$_3$ | 3.89 | 3 |
| 12 | Cl | H | 1 | 3-Cl | 3.75 | 4 |
| 13 | Cl | H | 1 | 4-OCF$_3$ | 4.08 | 3 |
| 14 | Cl | H | 1 | 4-SCH$_3$ | 3.75 | 3 |
| 15 | Cl | H | 1 | 4-F | 3.40 | 3 |
| 16 | Br | H | 1 | 4-Br | 3.91 | 3 |
| 17 | Br | H | 1 | 4-CF$_3$ | 3.94 | 3 |
| 18 | Br | H | 1 | 3-Cl | 3.78 | 4 |
| 19 | Br | H | 1 | 4-OCF$_3$ | 4.08 | 3 |
| 20 | Br | H | 1 | 4-SCH$_3$ | 3.78 | 3 |
| 21 | Br | H | 1 | 4-F | 3.42 | 3 |
| 22 | CH$_3$ | H | 1 | 4-Br | 3.86 | 3 |
| 23 | CH$_3$ | H | 1 | 4-CF$_3$ | 3.86 | 3 |
| 24 | CH$_3$ | H | 1 | 3-Cl | 3.72 | 4 |
| 25 | CH$_3$ | H | 1 | 4-OCF$_3$ | 4.03 | 3 |
| 26 | CH$_3$ | H | 1 | 4-SCH$_3$ | 3.72 | 3 |
| 27 | I | H | 1 | 4-Br | 4.00 | 3 |
| 28 | I | H | 1 | 4-CF$_3$ | 4.03 | 3 |
| 29 | I | H | 1 | 3-Cl | 3.86 | 4 |
| 30 | I | H | 1 | 4-OCF$_3$ | 4.21 | 3 |
| 31 | I | H | 1 | 4-SCH$_3$ | 3.86 | 3 |
| 32 | I | H | 1 | 4-F | 3.55 | 3 |
| 33 | CF$_3$ | H | 2 | 3,4-F$_2$ | 3.55 | 1 |
| 34 | CF$_3$ | H | 2 | 3-F, 4-Cl | 3.76 | 1 |
| 35 | CF$_3$ | H | 2 | 3-Cl, 4-F | 3.81 | 1 |
| 36 | CF$_3$ | H | 2 | 2,4-F$_2$ | 3.41 | 1 |
| 37 | CF$_3$ | H | 2 | 3-F, 4-OCF$_3$ | 4.08 | 1 |
| 38 | CF$_3$ | H | 2 | 3-CF$_3$, 4-Cl | 4.18 | 1 |
| 39 | CF$_3$ | H | 2 | 3-CF$_3$, 4-CH$_3$ | 4.18 | 1 |
| 40 | CF$_3$ | H | 2 | 3-CF$_3$, 4-OCF$_3$ | 4.41 | 1 |
| 41 | CF$_3$ | H | 2 | 3-CF$_3$, 4-F | 3.90 | 1 |
| 42 | CF$_3$ | H | 2 | 3-CH$_3$, 4-Cl | 4.18 | 1 |
| 43 | CF$_3$ | H | 2 | 3,5-Cl$_2$ | 4.16 | 1 |
| 44 | I | H | 2 | 3,4-Cl$_2$ | 4.06 | 1 |
| 45 | CF$_3$ | H | 2 | 2-F, 4-Cl | 3.68 | 1 |
| 46 | I | H | 1 | 4-Cl | 3.74 | 3 |
| 47 | CF$_3$ | 5'-F | 2 | 3,4-Cl$_2$ | 4.11 | 1, 2 |
| 48 | CF$_3$ | 3'-F | 2 | 3,4-Cl$_2$ | 3.81 | 1, 2 |

TABLE 1-continued (I)

| No. | R$^1$ | R$^2$ | m | R$^3$ | logP (pH 2.3) | Group |
|---|---|---|---|---|---|---|
| 49 | Cl | H | 1 | 4-Cl | 3.64 | 3 |
| 50 | Br | H | 1 | 4-Cl | 3.66 | 3 |

Preparation of Starting Materials of the Formula (III)

Examples (III-1)

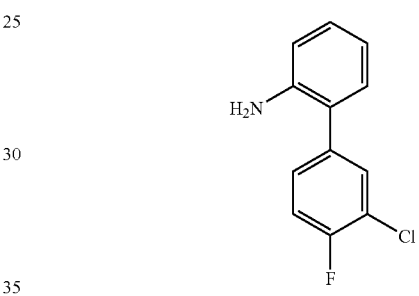

Under an atmosphere of argon, 38.8 g (223 mmol) of 3-chloro-4-fluorophenylboronic acid and 40.6 g (186 mmol) of 2-iodoaniline are dissolved in 220 ml of toluene, 22 ml of ethanol and 45 ml of a 4 M sodium bicarbonate solution. 4.3 g (4 mmol) of tetrakis(triphenylphosphine)palladium(0) are added, and the reaction solution is heated at 80° C. for 2–16 h. For work-up, the phases are separated and the organic phase is dried over magnesium sulphate and concentrated. The crude product is purified by column chromatography (cyclohexane/ethyl acetate 3:1) and/or by recrystallization.

This gives 19.8 g (48% of theory) of 3'-chloro-4'-fluoro-1,1'-biphenyl-2-amine of logP (pH 2.3)=3.01.

Preparation of Starting Materials of the Formula (IV)

Example (IV-1)

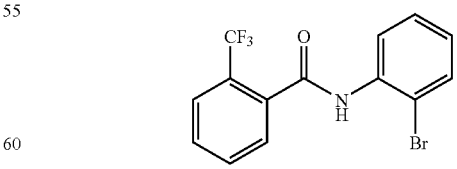

7.5 g (0.044 mol) of 2-bromaniline are initially charged in 100 ml of acetonitrile, and 7.8 g (0.057 mol) of potassium carbonate and 10.0 g (0.048 mol) of 2-trifluoro-methylbenzoyl chloride are added in succession. The reaction solution is heated under reflux for 16 h. For work-up, the solution is concentrated and the residue is chromatographed on silica gel using cyclohexane/ethyl acetate.

This gives 9.75 g (65% of theory) of N-(2-bromophenyl)-2-(trifluoro-methyl)benzamide of logP (pH 2.3)=2.99.

The logP values given in the tables and preparation examples above are determined in accordance with EEC Directive 79/831 Annex V.48 by HPLC (High Performance Liquid Chromatography) on a reversed-phase column (C18). Temperature: 43° C.

The determination is carried out in the acidic range at pH 2.3 using the mobile phases 0.1% aqueous phosphoric acid and acetonitrile; linear gradient from 10% acetonitrile to 90% acetonitrile.

Calibration is carried out using unbranched alkan-4-ones (of 3 to 16 carbon atoms) with known logP values (determination of the logP values by the retention time using linear interpolation between two successive alkanones).

Use Examples

Example A

| Podosphaera test (apple)/protective | |
|---|---|
| Solvents: | 24.5 parts by weight of acetone |
| | 24.5 parts by weight of dimethylacetamide |
| Emulsifier: | 1.0 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of the apple mildew pathogen *Podosphaera leucotricha*. The plants are then placed in a greenhouse at about 23° C. and a relative atmospheric humidity of about 70%.

Evaluation is carried out 10 days after the inoculation. 0% means an efficacy which corresponds to that of the control, whereas an efficacy of 100% means that no infection is observed.

Active compounds, application rates and test results are shown in the table below.

TABLE A

*Podosphaera* test (apple)/protective

| | Active compound | Application rate of active compound in g/ha | Efficacy in % |
|---|---|---|---|
| 7 | 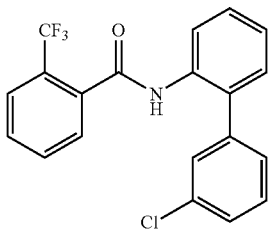 | 100 | 100 |
| 12 | 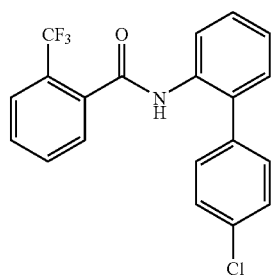 | 100 | 100 |
| 1 | 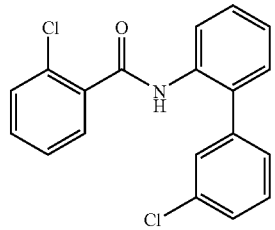 | 100 | 100 |
| 33 | 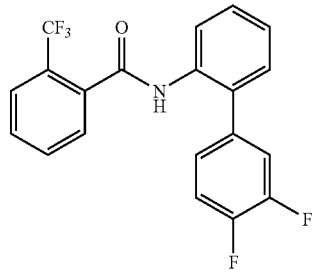 | 100 | 100 |
| 34 | 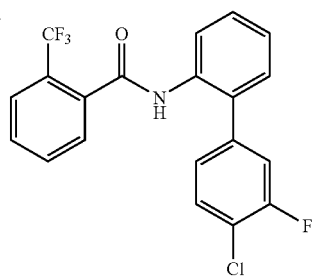 | 100 | 100 |
| 35 | 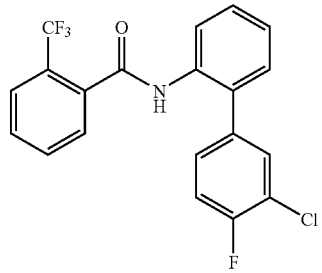 | 100 | 100 |

TABLE A-continued

Podosphaera test (apple)/protective

| Active compound | Application rate of active compound in g/ha | Efficacy in % |
|---|---|---|
| 4 (CF₃-benzamide-N-H-biphenyl-3,4-diCl) | 100 | 100 |
| 41 (CF₃-benzamide-N-H-biphenyl-3-CF₃-4-F) | 100 | 94 |
| 42 (CF₃-benzamide-N-H-biphenyl-3-CH₃-4-Cl) | 100 | 100 |
| 2 (CF₃-benzamide-N-H-biphenyl-2,4-diCl) | 100 | 100 |
| 3 (CF₃-benzamide-N-H-biphenyl-2-CH₃-4-Cl) | 100 | 99 |

Example B

| Sphaerotheca test (cucumber)/protective | |
|---|---|
| Solvents: | 24.5 parts by weight of acetone |
| | 24.5 parts by weight of dimethylacetamide |
| Emulsifier: | 1.0 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Sphaerotheca fuliginea*. The plants are then placed in a greenhouse at about 23° C. and a relative atmospheric humidity of about 70%.

Evaluation is carried out 7 days after the inoculation. 0% means an efficacy which corresponds to that of the control, whereas an efficacy of 100% means that no infection is observed.

Active compounds, application rates and test results are shown in the table below.

TABLE B

Sphaerotheca test (cucumber)/protective

| Active compound | Application rate of active compound in g/ha | Efficacy in % |
|---|---|---|
| 7 (CF₃-benzamide-N-H-biphenyl-3-Cl) | 100 | 100 |
| 1 (CF₃-benzamide-N-H-biphenyl-4-Cl) | 100 | 94 |
| 33 (CF₃-benzamide-N-H-biphenyl-3,4-diF) | 100 | 82 |

TABLE B-continued

*Sphaerotheca* test (cucumber)/protective

| Active compound | Application rate of active compound in g/ha | Efficacy in % |
|---|---|---|
| 34  2-CF₃-C₆H₄-C(O)NH-[2-(4-Cl-3-F-phenyl)phenyl] | 100 | 95 |
| 35  2-CF₃-C₆H₄-C(O)NH-[2-(4-F-3-Cl-phenyl)phenyl] | 100 | 93 |
| 4   2-CF₃-C₆H₄-C(O)NH-[2-(3,4-diCl-phenyl)phenyl] | 100 | 100 |
| 41  2-CF₃-C₆H₄-C(O)NH-[2-(4-F-3-CF₃-phenyl)phenyl] | 100 | 100 |
| 42  2-CF₃-C₆H₄-C(O)NH-[2-(4-Cl-3-CH₃-phenyl)phenyl] | 100 | 100 |
| 2   2-CF₃-C₆H₄-C(O)NH-[2-(2,4-diCl-phenyl)phenyl] | 100 | 94 |
| 3   2-CF₃-C₆H₄-C(O)NH-[2-(4-Cl-2-CH₃-phenyl)phenyl] | 100 | 100 |

Example C

*Venturia* test (apple)/protective

| Solvents: | 24.5 parts by weight of acetone |
| | 24.5 parts by weight of dimethylacetamide |
| Emulsifier: | 1.0 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the apple scab pathogen *Venturia inaequalis* and then remain in an incubation cabin at about 20° C. and 100% relative atmospheric humidity for 1 day.

The plants are then placed in a greenhouse at about 21° C. and a relative atmospheric humidity of about 90%.

Evaluation is carried out 10 days after the inoculation. 0% means an efficacy which corresponds to that of the control, whereas an efficacy of 100% means that no infection is observed.

Active compounds, application rates and test results are shown in the table below.

TABLE C

Venturia test (apple)/protective

| Active compound | | Application rate of active compound in g/ha | Efficacy in % |
|---|---|---|---|
| 7 | 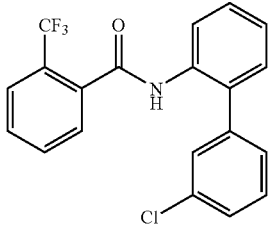 | 100 | 100 |
| 12 | 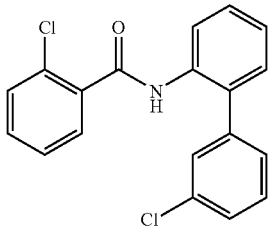 | 100 | 100 |
| 1 | 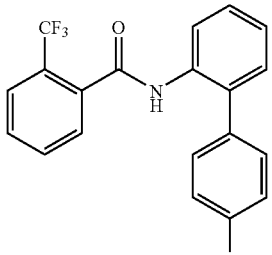 | 100 | 97 |
| 33 | 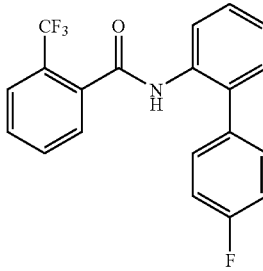 | 100 | 100 |
| 34 | 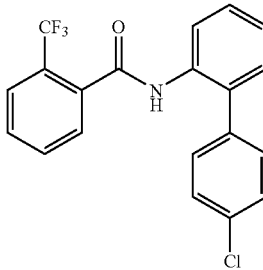 | 100 | 100 |

TABLE C-continued

Venturia test (apple)/protective

| Active compound | | Application rate of active compound in g/ha | Efficacy in % |
|---|---|---|---|
| 35 | 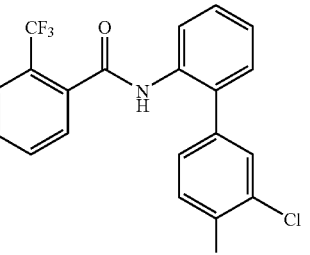 | 100 | 100 |
| 4 | 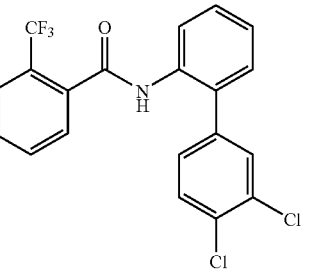 | 100 | 100 |
| 42 | 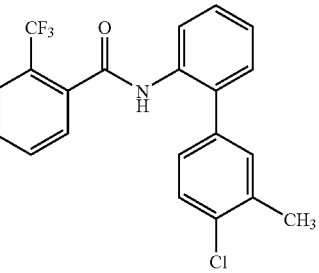 | 100 | 100 |
| 3 | 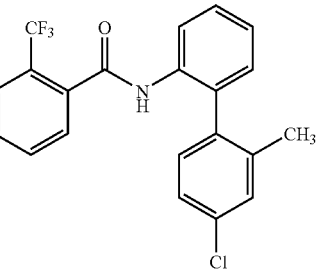 | 100 | 100 |

Example D

Pyrenophora teres test (barley)/protective

| Solvent: | 25 parts by weight of N,N-dimethylacetamide |
|---|---|
| Emulsifier: | 0.6 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of *Pyrenophora teres*. The plants remain in an incubation cabin at 20° C. and 100% relative atmospheric humidity for 48 hours.

The plants are then placed in a greenhouse at about 20° C. and a relative atmospheric humidity of about 80%.

Active compounds, application rates and test results are shown in the table below.

TABLE D

*Pyrenophora teres* test (barley)/protective

| Active compound | Application rate of active compound in g/ha | Efficacy in % |
|---|---|---|
| 7 (2-CF₃-benzamide-N-(3'-Cl-biphenyl-2-yl)) | 500 | 90 |
| 4 (2-CF₃-benzamide-N-(3',4'-diCl-biphenyl-2-yl)) | 500 | 100 |

Example E

| Alternaria test (tomato)/protective | |
|---|---|
| Solvent: | 49 parts by weight of N,N-dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young tomato plants are sprayed with the preparation of active compound at the stated application rate. 1 day after the treatment, the plants are inoculated with a spore suspension of *Alternaria solani* and are then kept at 100% relative atmospheric humidity and 20° C. for 24 h. The plants are then kept at 96% relative atmospheric humidity and a temperature of 20° C.

Evaluation is carried out 7 days after the inoculation. 0% means an efficacy which corresponds to that of the control, whereas an efficacy of 100% means that no infection is observed.

Active compounds, application rates and test results are shown in the table below.

TABLE E

*Alternaria* test (tomato)/protective

| Active compound | Application rate of active compound in g/ha | Efficacy in % |
|---|---|---|
| 5 (2-CF₃-benzamide-N-(4'-Br-biphenyl-2-yl)) | 750 | 94 |
| 7 (2-CF₃-benzamide-N-(3'-Cl-biphenyl-2-yl)) | 750 | 94 |
| 10 (2-Cl-benzamide-N-(4'-Br-biphenyl-2-yl)) | 750 | 92 |
| 18 (2-Br-benzamide-N-(3'-Cl-biphenyl-2-yl)) | 750 | 100 |
| 33 (2-CF₃-benzamide-N-(3',4'-diF-biphenyl-2-yl)) | 750 | 94 |

The invention claimed is:

1. A biphenylbenzamide derivative of formula (Ia)

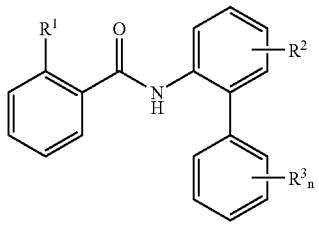

(Ia)

in which

R¹ represents methyl, trifluoromethyl, chlorine, bromine, or iodine,

R² represents hydrogen,

R³ represents halogen, cyano, nitro, $C_1$–$C_6$-alkyl, $C_1$–$C_4$-alkoxy, $C_1$–$C_4$-alkylthio, $C_1$–$C_4$-alkylsulphonyl, $C_2$–$C_6$-alkenyl, or $C_3$–$C_6$-cycloalkyl; or represents $C_1$–$C_6$-haloalkyl, $C_1$–$C_6$-haloalkoxy, $C_1$–$C_6$-haloalkylthio, or $C_1$–$C_6$-haloalkylsulphonyl having in each case 1 to 13 halogen atoms, and n represents 2, 3, 4, or 5, where the radicals R³ may be identical or different.

2. A composition for controlling unwanted microorganisms comprising one or more biphenylbenzamide derivatives of formula (Ia) according to claim 1 and one or more extenders and/or surfactants.

3. A process for preparing a composition for controlling unwanted microorganisms comprising mixing one or more biphenyl-benzamide derivatives of formula (Ia) according to claim 1 with one or more extenders and/or surfactants.

4. A method for controlling unwanted microorganisms comprising applying one or more biphenylbenzamide derivatives of formula (Ia) according to claim 1 to the microorganisms and/or their habitat, wherein the microorganisms are selected from the group consisting of *Xanthomonas* species, *Pseudomonas* species, *Erwinia* species, *Erysiphe* species, *Sphaerotheca* species, *Podosphaera* species, *Cochliobolus* species, *Uromyces* species, *Puccinia* species, *Tilletia* species, *Ustilago* species, *Pellicularia* species, *Leptosphaeria* species, and *Alternaria* species.

5. A method for controlling unwanted microorganisms according to claim 4 wherein the microorganisms are *Xanthomonas campestris* pv. *oryzae, Pseudomonas syringae* pv. *lachrymans, Erwinia amylovora, Sphaerotheca fuliginea, Podosphaera leucotricha, Cochliobolus sativus* (conidia form: Drechslera, syn: Helminthosporium), *Uromyces appendiculatus, Puccinia recondita, Tilletia caries, Ustilago nuda* or *Ustilago avenae, Pellicularia sasakii, Leptosphaeria nodorum,* or *Alternaria solani.*

* * * * *